United States Patent [19]

Petty-Weeks

[11] Patent Number: 4,812,594

[45] Date of Patent: Mar. 14, 1989

[54] PROCESS FOR PURIFICATION OF CRUDE P-HYDROXYMETHYLBENZOIC ACID

[75] Inventor: Bruce Petty-Weeks, West Chicago, Ill.

[73] Assignee: Amoco Corporation, Chicago, Ill.

[21] Appl. No.: 93,911

[22] Filed: Sep. 8, 1987

Related U.S. Application Data

[63] Continuation-in-part of Ser. No. 40,895, Apr. 21, 1987.

[51] Int. Cl.$^4$ .............................................. C07C 65/00
[52] U.S. Cl. .................................................... 562/473
[58] Field of Search ......................................... 564/473

[56] References Cited

U.S. PATENT DOCUMENTS 4,721,808  1/1988  Lillwitz ............................. 562/473

Primary Examiner—Paul J. Killos
Attorney, Agent, or Firm—William C. Clarke; William H. Magidson; Ralph C. Medhurst

[57] ABSTRACT

Aqueous solutions of crude p-hydroxymethylbenzoic acid are purified to relatively low levels of 4-carboxybenzaldehyde by hydrogenation in the presence of a nickel on kieselguhr catalyst. 4-carboxybenzaldehyde is hydrogenated to p-hydroxymethylbenzoic acid. Toluic acid production is minimal.

6 Claims, No Drawings

4,812,594

PROCESS FOR PURIFICATION OF CRUDE P-HYDROXYMETHYLBENZOIC ACID

This application is a continuation-in-part of Serial No. 040,895 filed on April 21, 1987.

FIELD OF THE INVENTION

This invention relates to a method of purifying hydroxymethyl aryl monocarboxylic acid compounds from monocarboxylic acid impurities in a catalyzed hydrogenation. More particularly, it relates to the selective reduction of 4-carboxybenzaldehyde in the presence of p-hydroxymethylbenzoic acid with a nickel catalyst to hydrogenate one aldehyde group to a hydroxymethyl group of the 4-carboxybenzaldehyde and yet is selective enough to prevent reduction of the carboxylic acid group of the 4-carboxybenzaldehyde and to prevent hydrogenolysis of the hydroxymethyl group of the p-hydroxymethylbenzoic acid which is also present.

BACKGROUND OF THE INVENTION p-Hydroxymethylbenzoic acid (pHMBA) is an important monomer for preparation of poly(p-methylenebenzoate). Poly(p-methylenebenzoate) is prepared from pHMBA by polymerization under polycondensation and melt polymerization conditions in the presence of a suitable catalyst.

Numerous methods are known for the preparation of p-hydroxymethylbenzoic acid. Among other methods, some of these are based on the saponification of a corresponding halogenmethyl compound, such as p-chloromethylbenzoic acid or the esters thereof or p-chloromethylbenzonitrile. For example, several methods for the synthesis of p-hydroxymethylbenzoic acid are taught in U.S. Pat. No. 4,130,719. The electrochemical reduction of terephthalic acid to p-hydroxymethylbenzoic acid is taught in commonly-assigned application Ser. No. 319,120, filed Nov. 9, 1981, now U.S. Pat. No. 4,381,229.

p-Hydroxymethylbenzoic acid must be free from by-products when it is to be employed in polycondensation reactions, such as in the preparation of polyesters. However, most of the known processes for the preparation of p-hydroxymethylbenzoic acid do not yield the acid free from by-products. Thus, for example, during the saponification of highly pure p-chloromethylbenzoic acid in a faintly alkaline aqueous medium, up to 10% of diben- zylether-4,4'-dicarboxylic acid is always produced.

In other methods, as for example, in the electrochemical reduction of terephthalic acid to p-hydroxymethylbenzoic acid many competing reactions take place in the electrolysis cell. The resulting presence of 4-carboxybenzaldehyde (4-CBA), dihydroxymethylbenzene, toluic acid and other impurities render the resulting p-hydroxymethylbenzoic acid undesirable for use as a monomer for polymer applications without further expensive purification.

It is well-known that in the cathodic reduction of carboxylic acids that two types of products can result, either the corresponding aldehyde in a two-electron process or the hydroxymethyl compound in a four-electron process where the aldehyde is further reduced to the alcohol. (M. Baizer, *Organic Electrochemistry*, Deker, N.Y. (1973), 414) The alcohol can be further reduced to the methyl group.

4-Carboxybenzaldehyde and p-toluic acid, both of which occur in the electrochemical reduction of terephthalic acid to p-hydroxymethylbenzoic acid, and residual terephthalic acid act as polymer chain stoppers in polymerization of p-hydroxymethylbenzoic acid to poly(p- methylenebenzoate).

From mathematical calculations, a combined level of above 0.3 (wt)% of monocarboxylic acid impurities, i.e., 4-carboxybenzaldehyde and p-toluic acid, will limit molecular weight of the polymer chain and give a polymer with inferior mechanical properties and an inherent viscosity of less than about 0.6 deciliters/gram (dl/g) in a 60/40 phenol/tetrachloroethane solvent at 30° C. An inherent viscosity of at least 0.6 dl/g is suitable for preparation of molded parts having a tensile impact strength of at least 100 psi, according to ASTM D-1822, and for preparation of fibers and films of poly(p-methylenebenzate).

Although residual terephthalic acid impurities in p-hydroxymethylbenzoic acid create a stoichiometric imbalance of hydroxyl and carboxylic acid units such that the resultant polymer has a predominance of carboxylic acid end groups, terephthalic acid can be incorporated into any location of the polymer chain with consequent limited weight development. As a result, higher levels of residual terephthalic acid impurity can be tolerated than levels of 4-carboxybenzaldehyde and p-toluic acid.

4-Carboxybenzaldehyde is a particularly undesirable impurity because it acts as a chain-stopper during polyesterification and can be present in significant quantities, in a ratio of about 2:1, to p-toluic acid, as taught in U.S. Pat. No. 3,850,983. Although 4-carboxybenzaldehyde is difficult to remove by physical means, it can be hydrogenated to toluic acid and other derivatives, but toluic acid also acts as a chain-stopper during polyesterification. Toluic acid can be efficiently removed by cooling and crystallizing crude p-hydroxymethylbenzoic acids containing it. 4-Carboxybenzaldehyde also can be reduced to the hydroxymethyl compound, i.e., p-hydroxymethylbenzoic acid, in an electrochemical process as is taught by Baizer, mentioned above, but reduction of terephthalic acid in an electrochemical process results in increased quantities of 4-carboxybenzaldehyde despite the concurrent hydrogenation of 4-carboxybenzaldehyde to p-hydroxymethylbenzoic acid.

Catalytic methods of hydrogenating 4-carboxybenzaldehyde typically result in the production of toluic acid. For example, in the purification of terephthalic acid containing 4-carboxybenzaldehyde by catalytic hydrogenation, U.S. Pat. No. 4,260,817 teaches that hydrogenation of terephthalic acid using a bimetallic catalyst of palladium and platinum converts 4-carboxybenzaldehyde to p-toluic acid.

The presence of impurities which can act as color bodies is also highly undesirable. Color may appear in the newly-manufactured p-hydroxymethylbenzoic acid or can develop on standing or exposure to elevated temperatures or actinic light. Such color-forming impurities are occluded in the acid crystals and carry over into resins made from the acids, reducing or obliterating the market value of the end product. In uses which require less attention to color, the fact that the product is white or near white will still render the product more desirable. The process of this invention is useful in reducing the presence of impurities which can affect the color of the acid produced thereby and consequently the color of the final resin.

A batch or continuous process has now been found for the hydrogenation of 4-carboxybenzaldehyde in the presence of p-hydroxymethylbenzoic acid wherein one aldehyde group is hydrogenated to a hydroxymethyl group using a nickel catalyst and yet is selective enough to prevent hydrogenolysis of the hydroxymethyl group of the p-hydroxymethylbenzoic acid to the methyl group and reduction of the second carboxylic acid to a hydroxymethyl group or to a methyl group. Potential color bodies can also be reduced. More specifically, a process has been found for the preparation of p-hydroxymethylbenzoic acid by the reduction of 4-carboxybenzaldehyde and potential color bodies in the presence of a nickel catalyst under relatively mild conditions wherein conversion of p-hydroxymethylbenzoic acid is minimal and selectivity to p-hydroxymethylbenzoic acid is within the range of from about 80% to 90%. Yields are accordingly within the range of about 90 (wt)% of 4-carboxybenzaldehyde present.

Unexpectedly, it has been found that a nickel catalyst has catalytic activity in aqueous solvent to selectively hydrogenate an ammonium or alkali metal or alkaline earth metal salt of 4-carboxybenzaldehyde to the equivalent salt of p-hydroxymethylbenzoic acid in yields of 90 (wt)% or better. Only the aldehyde group is reduced to the hydroxymethyl group.

Color level of the purified salt of p-hydroxymethylbenzoic acid in batch or continuous process can be controlled effectively by modulating the hydrogen concentration in the impure solution while it is undergoing hydrogenation, in the method of U.S. Pat. No. 4,626,598, which is incorporated by reference.

Accordingly, it is an object of this invention to purify p-hydroxymethylbenzoic acid containing 4-carboxybenzaldehyde by hydrogenating 4-carboxybenzaldehyde to p-hydroxymethylbenzoic acid without increasing the level of p-toluic acid present.

It is a further object of this invention to hydrogenate 4-carboxybenzaldehyde to p-hydroxymethylbenzoic acid, in the presence of p-hydroxymethylbenzoic acid wherein over-hydrogenation is controlled, as over-hydrogenation can produce not only p-toluic acid but also a number of hydrogenated aromatic products including cyclohexane and several hydrogenated aromatic acids such as 1,4 cyclohexanedicarboxylic acid.

It is a further object of this invention to prepare p-hydroxymethylbenzoic acid in a highly purified state.

It is a further object of this invention to prepare p-hydroxymethylbenzoic acid in a highly-purified state for polymerization to poly(p-methylenebenzoate), the said poly(p-methylenebenzoate) having an inherent viscosity of greater than 0.6 dl/g in a 60/40 phenol/tetrachloroethane solvent at 30° C.

SUMMARY OF THE INVENTION

A process is disclosed for purification of a salt of p-hydroxymethylbenzoic acid, in aqueous solution containing 4-carboxybenzaldehyde wherein said 4-carboxybenzaldehyde is selectively catalytically hydrogenated to p-hydroxymethylbenzoic acid in absence of overhydrogenation of said 4-carboxybenzaldehyde to p-toluic acid and of said salt of p-hydroxymethylbenzoic acid, and wherein catalyst for said process is nickel on kieselguhr.

DETAILS OF THE INVENTION

In the preparation of p-hydroxymethylbenzoic acid by electrochemical reduction of the terephthalic acid, the catholyte can comprise a weakly basic solvent such as water with a soluble ammonium salt and ammonia with terephthalic acid. The product is a crude ammonium salt of p-hydroxymethylbenzoic acid with a number of by-products, the ammonium salt of 4-carboxybenzaldehyde, the ammonium salt of toluic acid, and the ammonium salt of terephthalic acid. The crude product is partially purified by using the difference in water solubility of the terephthalic acid salt and the p-hydroxymethylbenzoic acid salt. The crude product in aqueous solution is filtered hot, within a temperature range of from about 75° C. to about 150° C. to remove the terephthalic acid salt. The mother liquor is then cooled to a temperature below 40° C., preferably below 25° C. The partially purified salt of p-hydroxymethylbenzoic acid in aqueous solution is thereupon further purified by hydrogenation of the 4-carboxybenzaldehyde ammonium salt to the ammonium salt of p-hydroxymethylbenzoic acid.

Catalytic hydrogenation of 4-carboxybenzaldehyde in aqueous solution using a nickel on kieselguhr catalyst surprisingly has been found to be highly selective in the products obtained. Thus in accordance with the invention, it has been found possible to reduce the presence of 4-carboxybenzaldehyde from approximately 5(wt)% of the cell product to less than 0.1 (wt)% of the crude reaction product by selectively hydrogenating the 4-carboxybenzaldehyde to p-hydroxymethylbenzoic acid. Additional toluic acid is not a product.

It is essential that the process is carried out in the presence of a solvent in which both the starting materials and the end products are sufficiently soluble. Solvents which may be used are polar solvents such as water and alcohols such as lower aliphatic monohydric alcohols, preferably containing from 1 to 8 carbon atoms, for example, methanol, cycloaliphatic alcohols such as cyclohexanol, polyhydric alcohols such as butanediol or glycerol. Solvents other than water or alcohols such as lower aliphatic monohydric and polyhydric alcohols are unsuitable because either starting materials or end products are not sufficiently soluble.

It is essential that solution be basic, of a pH greater than 7 to maintain the solubility of starting materials and end products. Ammonia or oxides of alkali metals or alkaline earth metals can be used to maintain the basic condition. Ammonia is preferred because crude product from electrochemical reduction of terephthalic acid is the ammonium salt.

It is essential that the hydrogenation reaction temperature be maintained below 75° C., preferably below 50° C. Above 75° C., the production of p-toluic acid is increased significantly. A temperature below 50° C. minimizes production of p-toluic acid to minimal levels.

It is essential that contact time of the crude aqueous solution of pHMBA with the catalyst be controlled within limits. A continuous process accordingly is preferable in that space velocity can be monitored. A space velocity (lbs pHMBA solution/lb catalyst/hr) of the aqueous pHMBA of less than about 5 hours$^{-1}$ results in significant production of p-toluic acid.

The use of catalysts other than nickel on kieselguhr has been found to be of little value in hydrogenation of 4-carboxybenzaldehyde to p-hydroxymethylbenzoic acid since toluic acid, an undesirable impurity in product for polymerization to poly(p-methylenebenzoate), is produced in greater quantity. In one example, toluic acid content of p-hydroxymethylbenzoic acid electrochemical cell product increased from 3800 parts per million (ppm) to 8700 ppm after hydrogenation using a palladium on carbon catalyst. Platinum catalysts can be used, but nickel on kieselguhr has been found to be more effective in reduction of 4-CBA than platinum catalysts at reaction temperatures of 50° C. or less. Platinum catalysts are also less advantageous economically because of the high cost of platinum catalysts. The use of nickel on kieselguhr as catalyst is accordingly essential in the process of the instant invention.

The catalyst is preferably used in a quantity of from 0.1(wt)% to 30(wt)% of the crude cell product from the electrochemical reduction of terephthalic acid, preferably from 2(wt)% to 20(wt)%, more preferably of from 3(wt)% to 10(wt)%.

In general, the hydrogen pressure employed during the process is not critical, but is preferably from about 50 psi to about 500 psi. The hydrogenation reaction temperature is critical. It is essential that the hydrogenation temperature is within the range of from about 15° C. to less than 75° C., preferably from about 15° C. to about 30° C., more preferably from about 15° C. to about 25° C. At hydrogenation reaction temperatures above 75° C., 4-carboxybenzaldehyde is hydrogenated substantially to toluic acid.

The catalyst, nickel on kieselguhr, can be a commercially available catalyst containing up to about 60(wt)% nickel on kieselguhr. A typical catalyst useful in this invented process is Calsicat No. E235TR nickel on kieselguhr. A kieselguhr substrate incorporating a promoter such as zirconium can be used but the presence of a promoter is not essential. Another catalyst useful in the invention is United Catalyst G-69, nickel on kieselguhr promoted by zirconium, United Catalysts, Inc., Newark, N.J.

It is postulated that the selective reduction of the carbonyl group to the hydroxymethyl group can even be carried out under hydrogen pressure slightly greater than atmospheric but increased product production is obtained with higher hydrogen pressures such as at 50 to 500 psig.

Since solubilities of p-hydroxymethylbenzoic acid and impurities in solvents depend upon the temperature at which the reaction takes place, and toluic acid production is increased by increased temperature, it is necessary to increase pressure to increase the rate of reaction in the reduction of the carbonyl group at temperatures below 75° C. As shown in the following table, solubilities of the respective compounds increase significantly with increase in temperature.

| Solubilities of pHMBA and Impurities in Water | | |
|---|---|---|
| | Solubility (g/100 ml H$_2$O) | |
| Compound | at 20° C. | at 100° C. |
| pHMBA | ~0.5 | ~10.0 |
| p-Toluic Acid | 0.02 | 0.22 |
| 4-CBA | <0.005 | ~0.25 |
| Terephthalic Acid | <0.005 | 0.03 |

Accordingly, reactor pressure conditions primarily depend upon the temperature at which the purification process is carried out. Inasmuch as the temperatures at which practical amounts of the impure p-hydroxymethylbenzoic acid may be dissolved are substantially above the normal boiling point of the solvent, the process pressures are necessarily above atmospheric pressure to maintain the solution in liquid phase. If the reactor is hydraulically full, the reactor pressure can be controlled by the feed pumping rate. If the reactor has a head space, the reactor pressure can be maintained by gaseous hydrogen alone or in admixture with an inert gas such as water vapor and/or nitrogen in the head space. The use of an inert gas in admixture with hydrogen also can provide an advantageous means for modulating the reactor hydrogen partial pressure, especially at relatively low hydrogen partial pressures. To this end, the inert gas preferably is admixed with hydrogen prior to introduction into the reactor. In general, the reactor pressure during hydrogenation can be in the range of about 50 to about 500 pounds per square inch gauge (psig), and usually is in the range of about 50 psig to about 200 psig.

The hydrogenation reactor can be operated in several models. For example, a predetermined liquid level can be maintained in the reactor and hydrogen can be fed in, for any given reactor pressure, at a rate sufficient to maintain the predetermined liquid level. The difference between the actual reactor pressure and the vapor pressure of the p-hydroxymethylbenzoic acid solution present is the hydrogen partial pressure in the reactor vapor space. Alternatively, if hydrogen is fed in admixture with an inert gas such as nitrogen, the difference between the actual reactor pressure and the vapor pressure of the pHMBA solution present is the combined partial pressure of hydrogen and the inert gas admixed therewith. In this case the hydrogen partial pressure can be calculated from the known relative amounts of hydrogen and inert gas present in the admixture.

In yet another operating mode the reactor can be filled with the pHMBA solution so as to provide no reactor vapor space. That is, the reactor can be operated as a hydraulically full system with dissolved hydrogen being fed to the reactor by flow control. In such an instance, the solution hydrogen concentration can be modulated by adjusting the hydrogen flow rate to the reactor. If desired, a pseudo-hydrogen partial pressure value can be calculated from the solution hydrogen concentration which, in turn, can be correlated with the hydrogen flow rate to the reactor.

In the operating mode where process control is effected by adjusting the hydrogen partial pressure, the hydrogen partial pressure in the reactor preferably is in the range of about 10 psi to about 200 psi, or higher, depending upon the service pressure rating of the reactor, the degree of combination of the impure pHMBA, the activity and age of the particular catalyst employed, and like processing considerations.

In the operating mode where process control is effected by adjusting directly the hydrogen concentration in the feed solution, the latter usually is less than saturated with respect to hydrogen and the reactor itself is hydraulically full. Thus an adjustment of the hydrogen flow rate to the reactor will result in the desired control of hydrogen concentration in the solution.

The process can be operated either by batch or continuous method. A continuous process is preferable. The presence of carbon monoxide in a 4-CBA hydrogenation reactor is recognized by the prior art to be a problem (see, for example, U.S. Pat. No. 4,201,872 to Kimura) because carbon monoxide is known to inhibit the activity of hydrogenation catalysts. The present process in a continuous process can avoid this problem, however, by maintaining conditions favorable to carbon monoxide generation away from the Pt/C catalyst layer, that is, by sweeping the produced carbon monoxide from the catalyst bed by an effluent stream.

In a continuous method, space velocity (lbs pHMBA solution/lb catalyst/hr) of the aqueous crude pHMBA solution through the catalyst bed is about $5^{-1}$ hours to about 25 hours$^{-1}$, preferably about 10 hours$^{-1}$ to about 15 hours$^{-1}$.

The catalyst carrier is kieselguhr derived from diatomite in the form of granules having a surface area of at least about 600 m$^2$/g (N$_2$; BET Method), preferably about 800 m$^2$/g to about 1500 m$^2$/g. Other porous supports or substrates cannot be used even if the surface area requirements are met. For example, 43(wt)% nickel on alumina (Calsicat E235TR) was unsatisfactory.

Catalyst metal loading on the carrier for nickel can be in the range of from about 0.1 weight percent to about 10 weight percent, based on the total weight of the catalyst, i.e., metal plus active carbon carrier, and calculated as elemental metal. Preferably the nickel metal loading is about 5 weight percent. Such catalysts are commercially available.

A suitable nickel-kieselguhr catalyst can be obtained, for example, from United Catalysts, Newark, N.J., under the designation "Nickel on Kieselguhr Granules (Code CG-5)." This nickel-kieselguhr catalyst has a BET;N$_2$ surface area of about 1,000 m$^2$/gram and a particle size of 4×8 mesh, U.S. Sieve Series. Other suitable nickel-kieselguhr catalysts of similar size and surface area are available from Johnson Matthey Inc., Seabrook, N.H., under the designation "Nickel 5% on Steam Activated Kieselguhr Granules, Anhydrous."

For conversion of 4-CBA to pHMBA, the stoichiometric hydrogen requirement is one mole of hydrogen for each mole of 4-CBA so converted. Preferably the amount of hydrogen supplied to the reaction is about two times that stoichiometrically required for the reaction.

Accordingly, the instant invention comprises a method for purification by hydrogenation of p-hydroxymethylbenzoic acid containing impurities comprising 4-carboxybenzaldehyde which comprises the steps of: (a) preparing a basic solution of said crude p-hydroxymethylbenzoic acid compound in a polar solvent wherein pH of said solution is greater than 7 to solubilize said compound; (b) passing hydrogen through said solution in the presence of a nickel catalyst upon a substrate of kieselguhr at a temperature of up to 75° C.; c) recovering said nickel catalyst by separation from said solution; and d) separating said p-hydroxymethylbenzoic acid from said solution by cooling said solution to effect crystallization. Separation of the nickel catalyst from the solution can be by filtration or by centrifuge or by any suitable means. Preferably, the said catalyst is nickel on a substrate carrier of active kieselguhr in the form of granules having a surface area of at least about 600 m$^2$/g (N$_2$; BET Method) and catalyst nickel loading is from about 0.1 weight percent to about 10 weight percent of metal plus active kieselguhr carrier, calculated as elemental metal. More preferably, the said process is a continuous process, said polar solvent is water, said catalyst is 5% by weight nickel metal upon an active kieselguhr, maximum hydrogenation temperature is 50° C., space velocity is within the range of from about 5 hours$^{-1}$ to about 25 hours$^{-1}$, and said crude p-hydroxymethylbenzoic acid compound is an ammonium salt. The instant invented process can also be operated in a batch method.

Without limiting the invention, the present invention is illustrated further by the following examples.

EXAMPLE 1

The ability of a nickel on kieselguhr-promoted by zirconium (United Catalysts, Inc., G-69) catalyst to convert 4-CBA to pHMBA without increasing the level of toluic acid was tested.

A 300ml autoclave reactor was charged with 100ml of an aqueous solution of ammonium salts of p-hydroxymethylbenzoic acid (11.6 wt. %), terephthalic acid (1.3 wt. %), 4-carboxybenzaldehyde (13wt. %), and p-toluic acid (0.01 wt. %). pH was basic enough to obtain complete solution of the crude electrochemical cell product. A catalyst charge of 1.0g of 5% nickel on kieselguhr (G-69) was added, the reactor sealed, flushed with nitrogen, and the reactor filled to 50 psig with hydrogen. Stirring was initiated while maintaining the temperature inside the reactor at 50° C. After 3 hours, High Pressure L.C. analysis indicated that 99% of the 4-CBA had been converted to p-HMBA, but the p-toluic acid level increased by 35%.

EXAMPLE II

This example shows the effect of space velocity upon the production of p-toluic acid from ammonium 4-CBA in the presence of a nickel on kieselguhr catalyst (United G-69). Seven runs were made in the procedure of Example I, but in a continuous method. Space velocities of from 9 lbs pHMBA/lb catalyst/hr to 1 1/2 lbs pHMBA/lb catalyst/hr were used. Decreased space velocity increased production of p-toluic acid to undesirable levels. Results are in Table I.

TABLE I

Continuous Hydrogenation of Ammonium 4-CBA Nickel in Kieselguhr Catalyst

| Run No. | T °C. | Pressure psig | Space Velocity | 4-CBA Converted % | Selectivity p-toluic Acid In Product |
|---|---|---|---|---|---|
| 161 | 100 | 150 | 9 | 91 | 3.50 |
| 162 | 50 | 50 | 9 | 69 | 0.13 |
| 163 | 50 | 100 | 9 | 69 | 0.15 |
| 164 | 50 | 150 | 9 | 71 | 0.08 |
| 166 | 50 | 150 | 6 | 83 | 0.08 |
| 167 | 50 | 150 | 3 | 96 | 0.84 |
| 168 | 50 | 150 | 1.5 | 97 | 2.66 |

The above data also indicate the effect of a reaction temperature above 50° C. upon the production of p-toluic acid. Pressure has little effect.

Notes:
(a) Catalyst was United G-69.
(b) Solids contact, liquid feed on catalyst, was 1.5 g/ml.
(c) Selectivity based on moles of p-toluic acid produced/mole of 4-CBA reduced.
(d) pH of aqueous pHMBA solution was 8.5-9.
(e) Aqueous pHMBA solution was 16% concentration of which 98% solids was pHMBA.

EXAMPLE III In a batch procedure, five runs were made to compare the activity of a nickel on kieselguhr catalyst, or nickel on alumina catalyst, and three platinum catalysts on selectivity of hydrogenating ammonium 4-CBA to p-toluic acid. The nickel on kieselguhr catalyst showed significantly better results over the other catalysts. Results are in Table II.

TABLE II

Effect of Nickel and Platinum Catalysts In Hydrogenation of Ammonium 4-CBA at 50° C. and 100 psig

| Run No. | Catalyst | 4-CBA Conversion % | % p-toluic Acid Selectivity |
|---|---|---|---|
| 191 | Ni—Kieselguhr (United G-69) | 99 | 0.01 |
| 188 | Ni—Alumina (Calsicat E-255 TR) | 65 | 0.01 |
| 151 | 0.5 (wt) % Pt—Al$_2$O$_3$ (Englehard Extrudate) | 99 | 0.03 |
| 150 | 0.5 (wt) % Pt—Al$_2$O$_3$ (Metpros Sphere) | 61 | 0.05 |
| 138 | 0.5 (wt) % Pt—Al$_2$O$_3$ (Strem 78-1640) | 54 | 0.07 |

The above data indicate the superiority of a nickel on kiesulguhr catalyst in hydrogenating ammonium 4-CBA. Selectivity to p-toluic acid using a nickel on kieselguhr catalyst is significantly lower than other catalysts, including platinum catalysts, at the same temperature and pressure of 50° C. and 100 psig.

What is claimed is:

1. A method for purification by hydrogenation of p-hydroxymethylbenzoic acid containing impurities comprising 4-carboxybenzaldehye which comprises the steps of:
   (a) preparing a basic solution of said crude p-hydroxymethylbenzoic acid compound in a polar solvent wherein pH of said solution is greater than 7 to solubilize said compound;
   (b) passing hydrogen through said solution in the presence of a nickel catalyst upon a substrate of active kieselguhr in the form of granules having a surface area of at least about 600 m$^2$/g (N$_2$; BET Method), at a temperature of up to 75° C.;
   (c) recovering said nickel catalyst by separation from said solution; and
   (d) separating said p-hydroxymethylbenzoic acid from said solution by cooling said solution to effect crystallization.

2. The process of claim 1 wherein said catalyst is nickel on a substrate carrier of active kieselguhr in the form of granules having a surface area of at least about 600 m$^2$/g (N$_2$; BET Method) and catalyst nickel loading is from about 0.1 weight percent up to about 60 weight percent of metal plus active kieselguhr carrier, calculated as elemental metal.

3. The process of claim 2 wherein said nickel loading is about 5 weight percent of metal plus active kieselguhr carrier, calculated as elemental metal.

4. The process of claim 1 wherein said process is a continuous process, said polar solvent is water, said catalyst is 5% by weight nickel metal upon an active kieselguhr, maximum hydrogenation temperature is 50° C., and space velocity is within the range of from about 5 hours$^{-1}$ to about 25 hours$^{-1}$.

5. The process of claim 1 wherein said process is a batch process.

6. The process of claim 1 wherein said crude p-hydroxymethylbenzoic acid compound is an ammonium salt.

* * * * *

UNITED STATES PATENT OFFICE
CERTIFICATE OF CORRECTION

Patent No. 4,812,594          Dated March 14, 1989

Inventor(s) Petty-Weeks

It is certified that error appears in the above-identified patent and that said Letters Patent are hereby corrected as shown below:

| Column | Line | |
|---|---|---|
| 1 | 50 | "diben- zylether" should read --dibenzylether-- |
| 7 | 3 | "$5^{-1}$ hours" should read --5 hours$^{-1}$-- |
| 8 | 12 | "(13wt.%)," should read --(1.3 wt.%) |
| 8 | 22 | "p-HMBA" should read --pHMBA-- |
| 9 | 1 | "EXAMPLE III In a batch" should read --EXAMPLE III In a batch-- |
| 9 | 26 | "kjesulguhr" should read --kieselguhr-- |
| 10 | 18 | "$N^2$;" should read --$N_2$;-- |

Signed and Sealed this

Twentieth Day of June, 1989

Attest:

DONALD J. QUIGG

Attesting Officer          Commissioner of Patents and Trademarks